US008792987B2

(12) United States Patent
Stevenson et al.

(10) Patent No.: US 8,792,987 B2
(45) Date of Patent: *Jul. 29, 2014

(54) SATELLITE THERAPY DELIVERY SYSTEM FOR BRAIN NEUROMODULATION

(71) Applicant: Greatbatch Ltd., Clarence, NY (US)

(72) Inventors: Robert A. Stevenson, Canyon Country, CA (US); Christine A. Frysz, Orchard Park, NY (US); Barry C. Muffoletto, Alden, NY (US); Robert W. Siegler, Williamsville, NY (US); Steven W. Winn, Lancaster, NY (US); Thomas A. Skwara, Orchard Park, NY (US); Dominick J. Frustaci, Williamsville, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,268

(22) Filed: Apr. 8, 2013

(65) Prior Publication Data
US 2013/0226262 A1 Aug. 29, 2013

Related U.S. Application Data

(63) Continuation of application No. 12/619,551, filed on Nov. 16, 2009, now Pat. No. 8,442,644.

(60) Provisional application No. 61/115,765, filed on Nov. 18, 2008.

(51) Int. Cl.
*A61N 1/36* (2006.01)
*A61N 1/372* (2006.01)

(52) U.S. Cl.
CPC ........ *A61N 1/36135* (2013.01); *A61N 1/37288* (2013.01); *A61N 1/37282* (2013.01); *A61N 1/36082* (2013.01)

USPC .............. 607/45; 607/60; 607/115; 607/116; 607/118; 607/139

(58) Field of Classification Search
USPC ............. 607/1–2, 45, 60, 115–116, 118, 139
See application file for complete search history.

(56) References Cited

U.S. PATENT DOCUMENTS

| 4,991,582 A | 2/1991 | Byers et al. |
| 5,713,922 A | 2/1998 | King |

(Continued)

FOREIGN PATENT DOCUMENTS

WO 2007118194 10/2007

OTHER PUBLICATIONS

European Search Report; Jan. 25, 2010, EP09176342.

*Primary Examiner* — Deborah Malamud
(74) *Attorney, Agent, or Firm* — Michael F. Scalise

(57) ABSTRACT

Deep brain electrodes are remotely sensed and activated by means of a remote active implantable medical device (AIMD). In a preferred form, a pulse generator is implanted in the pectoral region and includes a hermetic seal through which protrudes a conductive leadwire which provides an external antenna for transmission and reception of radio frequency (RF) pulses. One or more deep brain electrode modules are constructed and placed which can transmit and receive RF energy from the pulse generator. An RF telemetry link is established between the implanted pulse generator and the deep brain electrode assemblies. The satellite modules are configured for generating pacing pulses for a variety of disease conditions, including epileptic seizures, Turrets Syndrome, Parkinson's Tremor, and a variety of other neurological or brain disorders.

28 Claims, 10 Drawing Sheets

(56) References Cited

U.S. PATENT DOCUMENTS

| | | |
|---|---|---|
| 5,938,688 A | 8/1999 | Schiff |
| 6,016,449 A | 1/2000 | Fischell et al. |
| 6,411,854 B1 | 6/2002 | Tziviskos et al. |
| 6,564,106 B2 | 5/2003 | Guck et al. |
| 6,615,074 B2 | 9/2003 | Mickle et al. |
| 6,618,623 B1 | 9/2003 | Pless et al. |
| 6,787,268 B2 | 9/2004 | Koke et al. |
| 6,920,359 B2 | 7/2005 | Meadows et al. |
| 7,151,961 B1 | 12/2006 | Whitehurst et al. |
| 7,346,391 B1 | 3/2008 | Osorio et al. |
| 7,363,090 B2 | 4/2008 | Halperin et al. |
| 2002/0099412 A1 | 7/2002 | Fischell et al. |
| 2005/0003268 A1 | 1/2005 | Scott et al. |
| 2005/0021107 A1 | 1/2005 | Firlik et al. |
| 2005/0165458 A1 | 7/2005 | Boveja et al. |
| 2005/0283210 A1 | 12/2005 | Blischak et al. |
| 2006/0095088 A1 | 5/2006 | De Ridder |
| 2006/0129206 A1 | 6/2006 | Merfeld et al. |
| 2006/0293723 A1 | 12/2006 | Whitehurst et al. |
| 2007/0112398 A1 | 5/2007 | Stevenson et al. |
| 2007/0225773 A1 | 9/2007 | Shen et al. |
| 2007/0247786 A1 | 10/2007 | Aamodt et al. |
| 2007/0260294 A1 | 11/2007 | Schulman et al. |
| 2007/0293915 A1 | 12/2007 | Kilgore et al. |
| 2007/0299480 A1 | 12/2007 | Hill |
| 2007/0299483 A1 | 12/2007 | Strother et al. |
| 2008/0021972 A1 | 1/2008 | Huelskamp et al. |
| 2008/0033490 A1 | 2/2008 | Giftakis et al. |
| 2008/0049376 A1 | 2/2008 | Stevenson et al. |
| 2008/0065181 A1 | 3/2008 | Stevenson |
| 2008/0071313 A1 | 3/2008 | Stevenson et al. |
| 2008/0086185 A1 | 4/2008 | Amurthur et al. |
| 2008/0116997 A1 | 5/2008 | Dabney et al. |
| 2008/0119919 A1 | 5/2008 | Atalar et al. |
| 2008/0132987 A1 | 6/2008 | Westlund et al. |
| 2008/0154331 A1 | 6/2008 | John et al. |
| 2008/0161886 A1 | 7/2008 | Stevenson et al. |
| 2008/0183247 A1 | 7/2008 | Harding |
| 2008/0228270 A1 | 9/2008 | Dahlberg |
| 2008/0300659 A1 | 12/2008 | Matos |
| 2009/0030488 A1 | 1/2009 | Bruinsma |
| 2009/0088826 A1 | 4/2009 | Bedenbaugh |
| 2009/0105784 A1 | 4/2009 | Massoud-Ansari et al. |
| 2009/0192569 A1 | 7/2009 | Llinas et al. |
| 2009/0240308 A1 | 9/2009 | Feher |
| 2009/0253977 A1 | 10/2009 | Kipke et al. |
| 2009/0281597 A1 | 11/2009 | Parramon et al. |
| 2009/0319000 A1 | 12/2009 | Firlik et al. |
| 2010/0030287 A1 | 2/2010 | Jaax et al. |

US 8,792,987 B2

SATELLITE THERAPY DELIVERY SYSTEM FOR BRAIN NEUROMODULATION

CROSS-REFERENCE TO RELATED APPLICATIONS

This application is a continuation of U.S. patent application Ser. No. 12/619,551, filed Nov. 16, 2009, now U.S. Pat. No. 8,442,644 to Stevenson et al., which claims priority from U.S. Provisional Patent Application Ser. No. 61/115,765, filed Nov. 18, 2008.

FIELD OF INVENTION

The control module typically includes telemetry for wirelessly communicating with an external programmer or network to permit transmission of patient data which may include, for example, GPS data, current or historical/sensed patient biologic data, or current or historical therapy delivery data. This invention relates to systems for brain neuromodulation electromagnetic therapy delivery. In particular, a satellite therapy delivery system for brain neuromodulation includes a control module having an RF transmitter or transceiver, and a remote satellite brain stimulation and/or sensing (SBS) module having biologic stimulating and/or sensing electrodes, a power source, and an RF receiver or transceiver for open or closed looped wireless communication with the control module.

BACKGROUND OF THE INVENTION

Deep brain stimulation (DBS) electrodes and/or shallow electrodes including subcutaneous or sub-dural electrodes are typically connected to one or more active implantable medical devices (AIMD) which provide various types of therapeutic pacing pulses for treating a variety of disease conditions including, but not limited to, epileptic seizures, Turrets Syndrome, Parkinson's Tremor, and a variety of other neurological or brain disorders. Typically these therapy delivery systems involve one or more DBS and/or shallow electrodes that are implanted into or adjacent to the brain matter (through a skull burr hole) with leadwires tunneled to an implanted hermetically sealed electronics module that applies the appropriate electrical therapy. Electrodes implanted deeply within the brain can be unipolar, bipolar, quadpolar, or multipolar, having many channels. Additional electrodes can be placed either subcutaneously or subdurally to create a multiplicity of electrical vectors through brain tissue.

By way of example, FIG. 1 is a side view of a human skull with two quadpolar DBS electrodes 20 and 20" placed deeply into the brain matter. There are leads 22, 22' connected to the deep brain electrodes 20, 20' and routed underneath the skin through a tunneling procedure along the back of the patient's head and down along the side of the patient's neck. In addition to the deep brain electrodes 20 and 20', there may also be subcutaneous or subdural electrodes 24 and 24" as shown. In this way, electrical stimulus may be between any of the electrodes or electrode pairs shown on the DBS electrodes 20 and 20' or between the DBS electrodes and the subcutaneous/subdural electrodes 24 and 24', as shown. This gives the physician a number of options in terms of electrical vectors for pacing pulses in the brain and for sensing various brain waves.

Leads 22 and 22' can each consist of a number (bundle) of coaxial or bi-filar leadwires. In this case, there are a sufficient number of leadwires to supply the two DBS quadpolar electrodes 20 and 20' (total of eight leadwires) in addition the quadpolar subcutaneous/subdural electrodes 24 and 24' (a total of eight more leadwires). Accordingly, in the illustrated embodiment, there are a total of sixteen leadwires that are encompassed within the encapsulated leads 22 and 22'.

FIG. 2 is an X-ray tracing of the front view of the pectoral area of the same patient shown in FIG. 1. Illustrated are two implantable pulse generators 26 and 26', which are typically housed in titanium cans. Since titanium does not show up that well on an X-ray, one can only see the outline of the titanium can, but can also see the internal circuit boards 28 and 28' inside the titanium housings very clearly. One can refer to prior art cardiac pacemakers for a better explanation of what these devices look like. One can also see the leads 22 and 22' whose proximal ends plug into connector blocks which are part of the implanted pulse generators 26 and 26', typically in accordance with AAMI Standards or ISO Standards, such as ISO IS1 or IS4. These leads can also be permanently connected via a hermetic seal without the need for an intermediary connector block.

FIG. 3 is a line drawing of the front view of the human head of FIG. 1, further showing by way of example the locations of the two prior art DBS electrodes 20 and 20'.

FIG. 4 illustrates the quadpolar electrodes 30 of the deep brain electrode 20, and also the associated multi-wire electrical lead 22 that, as previously mentioned, is routed between the skin 32 and the skull 34. A burr hole 36 is typically formed through the skull 34 to gain access for implantation of the DBS electrode assembly 20.

There are a number of problems associated with the prior art illustrated in FIGS. 1-4. One is the difficulty, due to the length of the leads 22 and 22', in routing the leads 22 and 22' from the pectorally implanted pulse generators 26 and 26' across the pectoral area of the chest, up the side of the neck and the back of the skull, and then finally down to the DBS electrodes 20 and 20'. Associated problems include the tendency for there to be infections, reliability issues due to lead breakage associated with the constant twisting, turning and bending of the head and neck area, as well as the fact that it has been well demonstrated that long leads can be problematic during medical diagnostic procedures, such as magnetic resonance imaging (MRI), U.S. Pat. No. 7,363,090 and U.S. Patent Publication Nos. 2007-0112398 A1, 2008-0071313 A1, 2008-0049376 A1, 2008-0132987 A1, 2008-0116997 A1, and 2008-0161886A1 are all incorporated herein by reference for an understanding of how the electromagnetic fields from MRI couple to implanted leads and can cause associated overheating and thermal injury.

There are also a number of problems associated with the surgical procedure involving tunneling of the leads under the skin and over torturous bends and surfaces. Not only are there issues of infection, the tunneling tools sometimes cause injury or poke through the skin and have other deleterious effects.

Moreover, there are general electromagnetic interference (EMI) problems associated with prior art implanted brain pulse generators or brain stimulators that also do sensing. The long leads 22 and 22' act as antennas and pick up stray electromagnetic signals from the patient environment. For example, electromagnetic emitters such as cellular telephones, microwave ovens, RFID readers and the like, can all induce signals on these leads which can disrupt the proper operation of the implanted pulse generator and/or its sensing signals.

There are additional problems associated with the relatively long electrical leads 22 and 22' that run from the implanted pulse generators 26 and 26' up to the location of the subdural electrodes 24' and the DBS electrodes 20 and 20', FIG. 5 is a top view of a sketch from an actual MRI slice taken through a patient's skull. In this case the MRI scanning of the patient was inadvertent. That is, the radiology technician was not aware of the presence of the deep brain stimulator. One can see an area 38 of a severe brain lesion that was caused by thermal injury during this 1.5 Tesla MRI procedure. This is a dramatic illustration of how the pulsed RF field produced by MRI equipment can overheat long implanted leads and how sensitive the brain is to thermal injury. This patient experienced severe neurologic disabilities due to this traumatic injury.

Accordingly, there is a need to eliminate, as much as possible, the associated lead wiring that runs from the implanted pulse generators 26 and 26' up to the location of the DBS electrodes 20 and 20'. The present invention addresses this need and provides other related advantages.

SUMMARY OF THE INVENTION

The present invention relates to a satellite therapy delivery system for brain neuromodulation which comprises, generally, a control module having an RF transmitter or transceiver, and a satellite brain stimulation and/or sensing (SBS) module including biologic stimulating and/or sensing electrodes, a power source, and an RF receiver or transceiver for wireless communication with the control module. The control module may be implanted within a patient's body at a location remote from the SBS module, or it may be externally worn by a patient having an implanted SBS module. The stimulating and/or sensing electrodes of the SBS module include a deep brain electrode, or subcutaneous or subdural paddle, patch or pad electrodes.

The control module and the SBS module may operate in an open loop communication mode or in a closed loop communication mode. The SBS module may comprise a plurality of SBS modules, each capable of independent wireless communication with the control module. Moreover, the SBS modules may be configured for independent wireless communication with each other.

The control module typically includes telemetry for wirelessly communicating with an external programmer or network to permit transmission of patient data which may include, for example, GPS data, current or historical sensed patient biologic data, or current or historical therapy delivery data.

The SBS module typically comprises a pulse generator and a power source. A bandstop filter may be associated with the stimulating and/or sensing electrodes or their associated leads. The SBS module further includes a processing circuit which is electrically coupled to the SBS module RF receiver or transceiver, and the power source. The processing circuit may include a protection diode array, and actuates the stimulating electrodes in response to a signal received from the control module. In a closed loop communication mode, the SBS module transmits sensed biologic data to the control module, the control module processes such biologic data to determine if therapy is required, and if therapy is required, the control module transmits actuation instructions to the SBS module. Such transmitted instructions include stimulation electrode actuation timing and wave shape instructions. The SBS module may transmit sensed biologic data to the control module at regular intermittent intervals, or only when predefined biologic data is detected.

Moreover, the SBS module comprises a biocompatible and hermetically sealed housing. The housing itself comprises a body, a removable cap, and a biocompatible O-ring having a leak rate of no more than $10^{-8}$ cubic centimeters per second.

The SBS housing body is fixed within a burr-hole through a patient's skull. Preferably, the cap of the SBS module housing is disposed generally coplanar with an outer surface of the patient's skull. A skin flap overlies the cap over the SBS module housing, which can be easily removed to gain access to the cap and, upon removal of the cap, to a battery within the housing. The SBS housing may be fixed to the patient's skull utilizing screws to prevent twisting of the SBS housing when the cap is removed. Moreover, the SBS module housing includes fixation tabs disposed within corresponding burr-hole recesses.

The SBS module housing may comprise a ceramic housing, and preferably an alumina ceramic housing. In this case, the leads for the electrodes and/or an antenna may extend directly through the housing without the requirement for a hermetic terminal. If the SBS housing is made of a more traditional biocompatible metal, a hermetic terminal is provided through which the antenna and/or leads for the electrodes extend.

A circuit board is disposed within the SBS housing, which includes a receiver or transceiver portion, and the circuit board is electrically coupled to the power source, the electrodes and an RF antenna. A protection diode array may be electronically coupled to the circuit board and/or the RF antenna. As discussed below, one or more of the electrodes may serve as the RF antenna.

In alternate embodiments, the SBS housing may include an exterior receptacle for an electrode lead plug. This permits electrical coupling between the electrode lead and the circuit board through the SBS housing.

The power source for the SBS module preferably comprises a replaceable battery module which is sealed within a biocompatible and hermetically sealed enclosure. This hermetically sealed battery module is itself disposed within the biocompatible and hermetically sealed housing of the SBS module.

Other features and advantages of the present invention will become apparent from the following more detailed description, taken in conjunction with the accompanying drawings which illustrate, by way of example, principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a satellite therapy delivery system for brain neuromodulation which effectively eliminates, as much as possible, the lead wiring that runs from the implanted pulse generator to the location of the brain stimulation and/or sensing electrodes. FIGS. 6 through 16 illustrate various apparatus and procedures for accomplishing the present invention. Also disclosed is a novel implantation approach for satellite brain stimulation module(s) which allows for multiple battery replacements without removing the stimulation module(s) or its associated electrodes. Battery replacement is as simple as injection of a local anesthetic and then incising and lifting a skull skin flap and then unscrewing or snapping open a hermetically sealed battery compartment.

Figure 1:
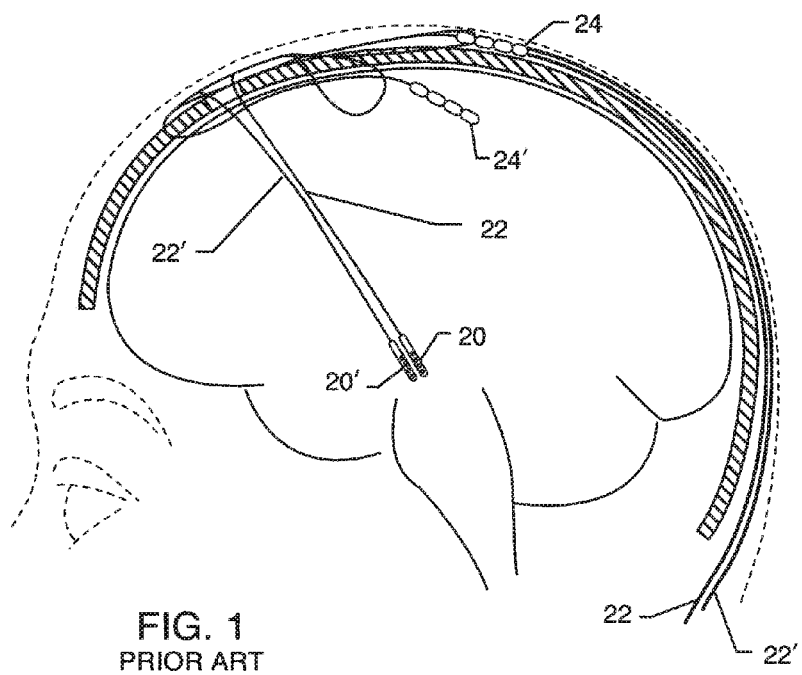
FIG. 1 is a side view of a human skull with two guadpolar brain stimulation electrodes placed deeply into the brain matter.
Figure 2:
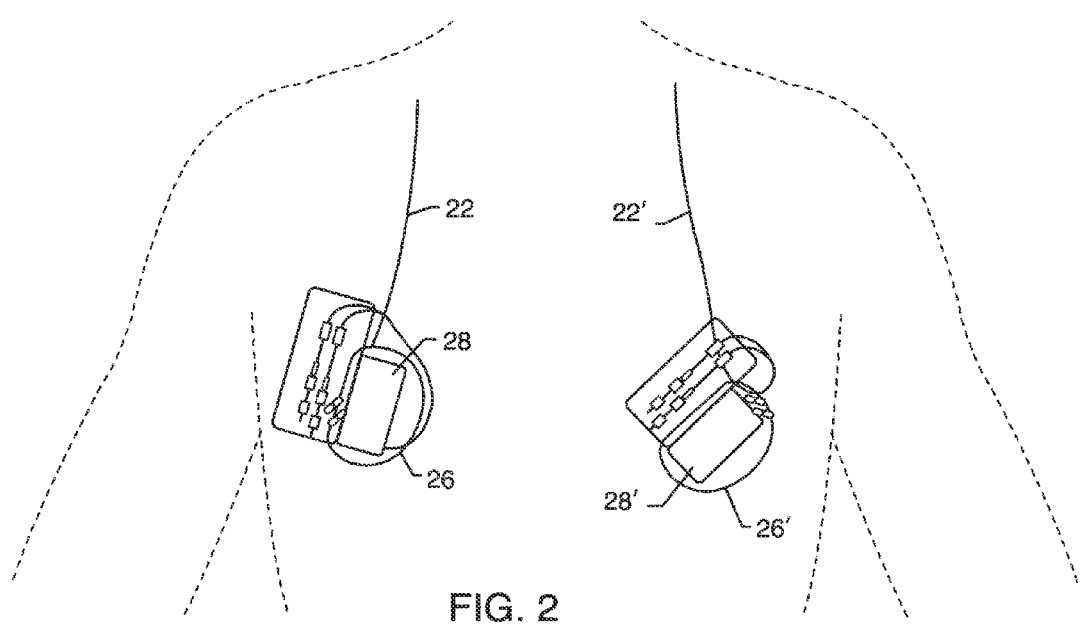
FIG. 2 is an X-ray tracing of the front view of the pectoral area of the same patient shown in FIG. 1, showing two implantable pulse generators.
Figure 3:
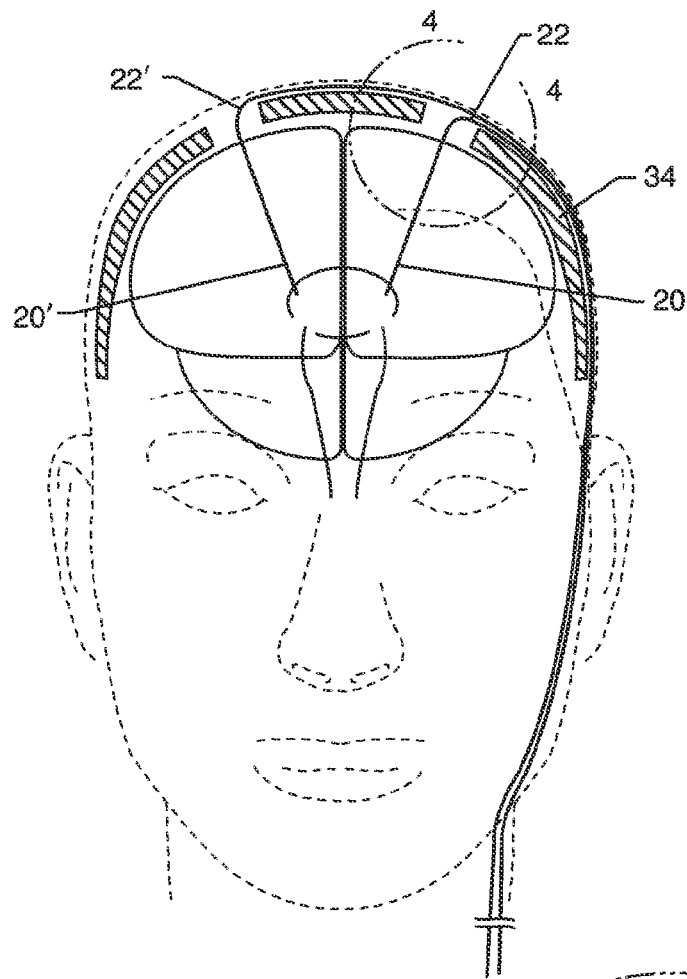
FIG. 3 is a line drawing of the front view of a human face showing two implanted prior art deep brain electrodes.
Figure 4:
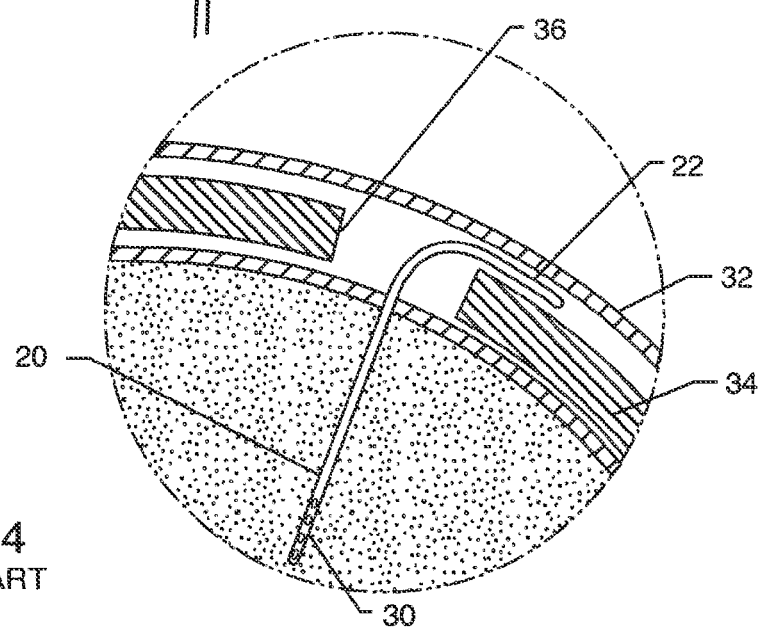
FIG. 4 is an enlarged fragmented sectional view of the area indicated by the line 1 in FIG. 3.
Figure 5:
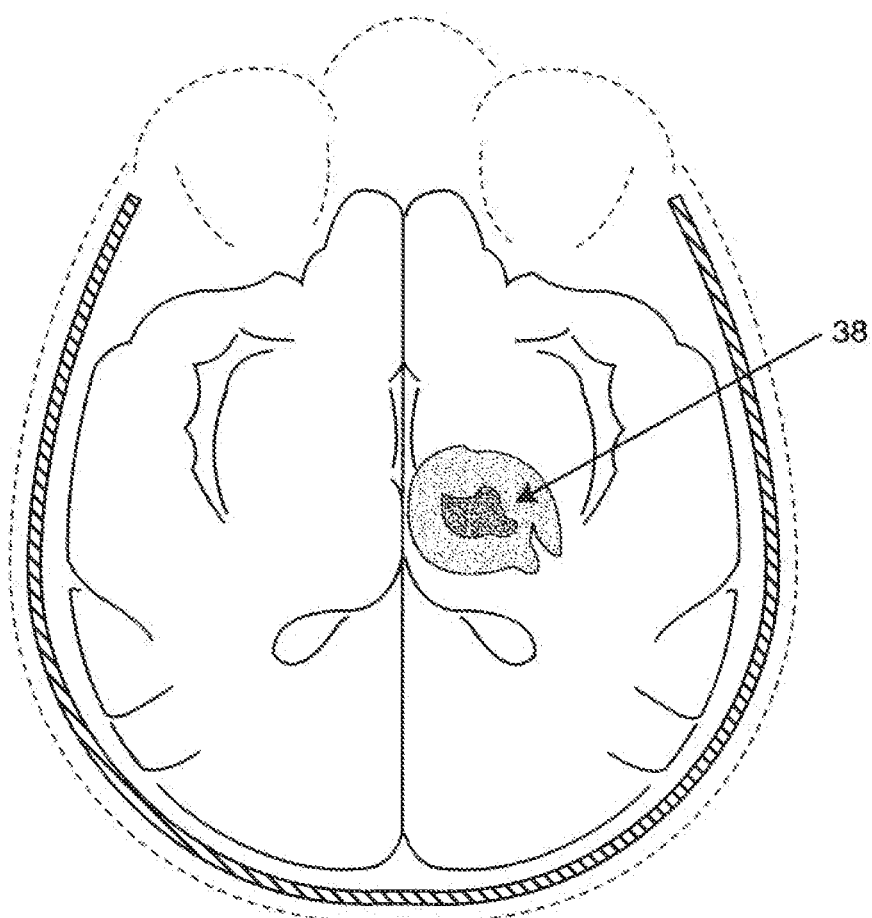
FIG. 5 is a top view of an MRI slice taken through a patient's skull that had a deep brain electrode implanted during an MRI procedure, and specifically showing an area of severe brain lesion caused by thermal injury.
Figure 6:
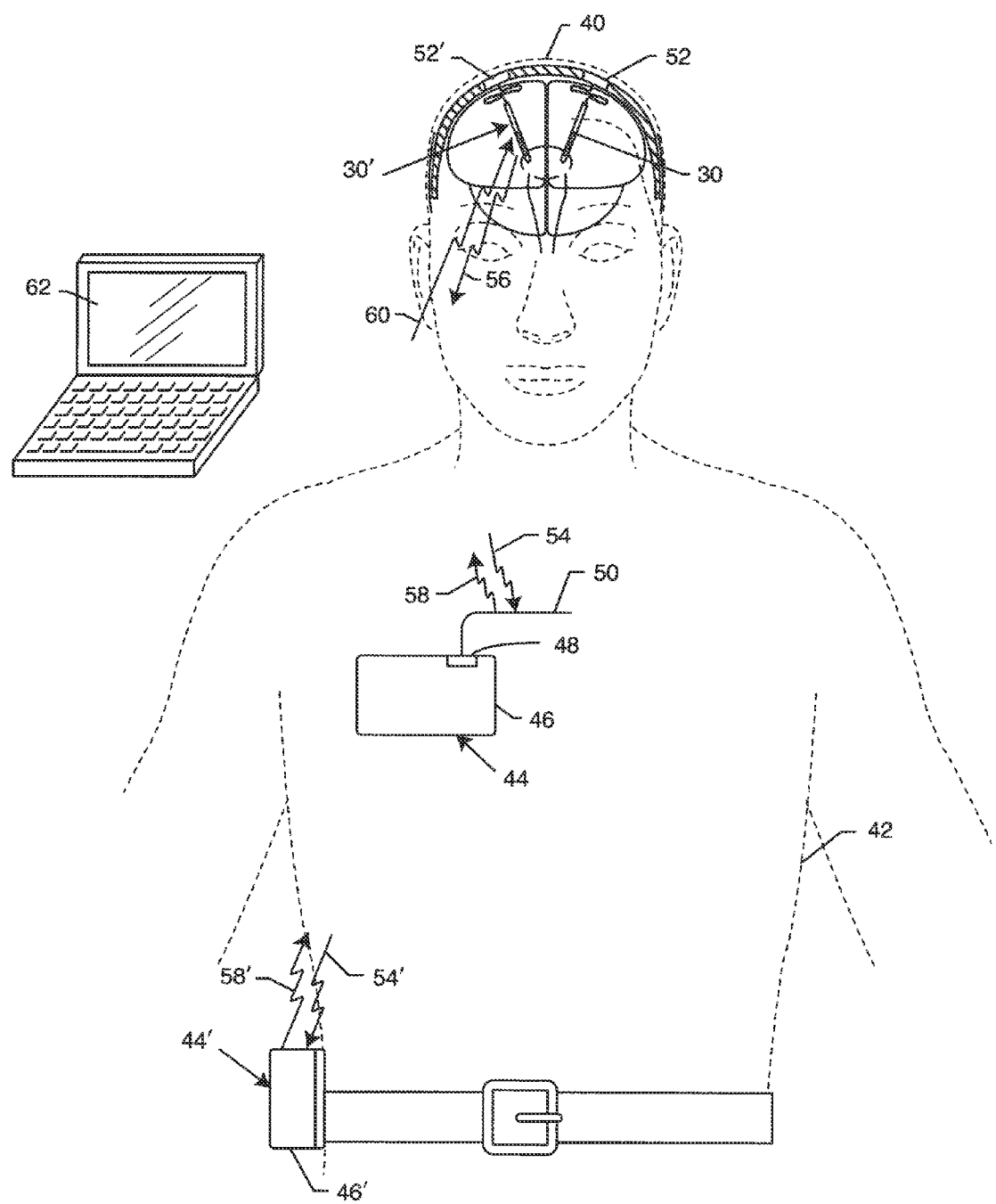
FIG. 6 is an outline drawing of a human head and torso, illustrating a satellite therapy delivery system incorporating the principles of the present invention.

FIG. 6 is an outline drawing of a human head 40 and torso 42. The satellite therapy delivery system of the present invention comprises a control module 44 that is typically implanted in the pectoral region in a manner very similar to a cardiac pacemaker or an implantable defibrillator. It can be implanted just under the skin, under the fatty layers or even under the pectoral muscle. In general, it will be housed in a titanium can 46 to protect its delicate electronic circuitry and battery from body fluids and moisture. The hermetically sealed can 46 also prevents any toxic materials that are associated with the electronic circuit board(s) or battery to leech out and contaminate body tissue. A unipolar or bipolar hermetic seal 48 is provided through which a conductive lead 50 extends. The purpose of this lead 50 is to provide an external antenna for transmission and reception of radio frequency (RF) pulses in accordance with the satellite pacing principles of the present invention. It will be appreciated that the implanted control module 44 could be placed at any other location that is convenient in the body, such as in the back or in the abdomen. The control module 44 could also be placed in a thicker area in the skull, for example, above the ear, or in another location in the skull or in any other area of thick bone (for example, the iliac crest). It could even be externally belt worn 44' in certain applications. The belt worn control module 44' could also be placed anywhere else on the body, for example, in a hand bag worn over the shoulder and so forth. It could even be placed on a table or a bedside night stand near the patient. It would be desirable, in some cases, that the externally worn control module 44 be water resistant. In this case, it wouldn't need to be totally hermetically sealed since it is not placed inside the body where it would be directly and continuously exposed to body fluids. However, if it were belt worn and was hermetically sealed, one could even go swimming with it.

Satellite brain stimulating and/or sensing (SBS) modules 52 and 52' are shown connected to and include quadpolar deep brain electrode assemblies 30 and 30'. These deep brain electrode assemblies 30 and 30' can also act as RF antennas which can transmit and receive RF energy to and from the control module 44. Accordingly, there is an RF telemetry link that is established between the implanted control module 44 and the SBS modules 52 and 52'.

The SBS modules 52 and 52' preferably contain their own power source (battery). Alternatively, they can capture energy by energy harvesting using chemical, thermal or external magnetic fields in a storage capacitor. In the simplest embodiment, the SBS modules 52 and 52' are triggered by RE pulses containing electronic instructions transmitted by the control module 44. The control module 44 and the SBS modules 52 and 52' form an RE telemetry subsystem that provides the wireless infrastructure needed to communicate measurement and control data within the human body. All nodes (44, 52 and 52') within the same system (implantable wireless network) are paired during a commissioning process whereby an association is made between nodes. What this means is that certain RE signals that are transmitted by the control module 44 are only received and processed by the SBS module 52 and other signals have a hand shake and are only received and processed by the SBS module 52'. Data communicated (messages) in this system are encrypted using a key that is common to all nodes in the same system, and is unique to each system. This makes the system inherently highly resistant or robust against electromagnetic interference from other outside electromagnetic signals. In other words, only an RF signal that has the correct encoding will be capable of triggering pulses in the SBS modules 52 and 52'. Messages in the system originate from a source node which can be either the control module 44 or either of the SBS modules 52 or 52', and terminate at a destination node. Some or all nodes may contain intermediary features that relay messages in one or more alternate routing patterns. In the preferred embodiment, the multiway routing capability provides redundancy needed for increased reliability. It will be apparent to those skilled in the art that this same system can be keyed to other satellite modules placed anywhere within the human body, such as for a spinal cord stimulator.

There are a number of frequencies that can be used for the RF telemetry subsystem. One is the designated medical implant communication service (MICS) frequency band. This band is from 402-405 MHz and is available for MICS operations on a shared, secondary basis. The Federal Communications Commission (FCC) determined that, compared to other available frequencies, the 402-405 MHz frequency band best meets the technical requirements for a number of reasons. First of all, the 402-405 MHz frequencies have propagation characteristics conducive to the transmission of radio signals within the human body. In addition, equipment designed to operate in the MICS band satisfies the requirement for human implant with respect to size, power, antenna performance, and receiver design. Furthermore, the MICS band is compatible with international frequency allocations. Moreover, the use of the MICS frequency band does not pose a significant risk of interference to other radio operations in that band. Finally, operation of MICS band is permitted by rule and without the need for individual license as issued by the FCC. For all these reasons, the MICS band is preferred for use in the present invention, although many other frequencies would also be suitable. The FCC is now considering a new RF frequency band that will be dedicated only to medical implants that will offer additional bandwidth. If this new frequency band is adopted, it will become the new preferred operating frequency band of the present invention.

The control module 44 has a number of very important features. First of all, being relatively larger than the relatively small SBS modules 52 and 52', it can have a much larger long-life power source (battery). Its battery can have primary battery chemistries that are common for implantable devices, such as lithium-iodine, lithium carbon monofloride, lithium-silver vanadium pentoxide, lithium manganese dioxide and the like. Secondary batteries (rechargeable) technologies can also be used, including but not limited to lithium-ion or other power storage devices, such as ultra capacitors or equivalent high-energy storage capacitors and the like.

For an externally worn device control module 44, alternate and less expensive battery technologies can also be used. These are commonly available in the consumer marketplace and include alkaline batteries, nickel metal hydride, NiCad, gel cells, carbon monofloride and manganese dioxide and liquid catho systems, including thionyl-chloride and sulfuryl-chloride. In addition, if the external control module 44 were worn in an appropriate location (for example, on the wrist or the ankle), various energy harvesting techniques could be used that depend upon the motion of the human body, such as mechanical energy harvesting, piezoelectric type mechanisms, or electromagnetic induction.

In addition to being belt worn, the external control module can also be worn as a type of necklace, a bracelet, an iPod-type holder on an arm band, in a vest, in a type of knapsack or backpack, or the like. The control module 44' could even be sitting on a desk, nightstand or a table next to the patient. The primary consideration here is that the externally worn control module 44' be close enough (within RF telecommunication range) to properly communicate with, and in a preferred embodiment create a closed loop communication system with, the remote SBS modules 52 and 52'. In the case where the external control module 44' has a secondary (rechargeable) battery, in addition to providing its communication functions whether sitting on a desk or table, it could also be conveniently recharged by being plugged into a wall charger, a solar type charger, or one that depends on movement or motion. In a preferred embodiment, one would have a convenient module on their stand that is plugged into the wall at all times with a convenient receptacle similar to those used for remote telephones when they are plugged in to their cradle to be recharged. Another advantage of the externally worn control module 44' is it can be fitted with controls that the patient can adjust. For example, for a patient that has a certain seizure, pain or tremor situation, he or she could control an adjustment knob or digital input (not shown) on the control module 44' thereby controlling the level of therapy. These various controls could also adjust the type of pulse, whether it be triangular, square wave, trapezoidal, rectangular, or other pulse shapes, the pulse repetition rate, and the like, that is being delivered to the electrodes 30 by the remote SBS modules 52 and 52'. For implanted control modules 44, the physician or patent can still communicate and adjust therapy via a close coupled (wanded telemetry) or a distant RF telemetry link.

The SBS modules 52 and 52' can each be either just a receiver and pulse generator, meaning that it will deliver pulses when instructed by the control module 44 (an open loop communication system), or, preferably, the SBS modules 52 and 52' will include transceivers to create a closed loop communication system with the controller module 44, which shall also have an RF transceiver. In other words, the satellite therapy delivery system of the present invention has two primary communication modes. In the open loop communication mode, the SBS module 52 does not do any sensing of brain electrical activity. The control module 44 is pre-programmed so that it sends controlled timing pulses to the SBS modules 52 and 52'. In an improved embodiment, the timing pulses would be preceded or include waveshape information so that the wave shape generator that is part of the SBS module 52 and/or 52' could produce the desired waveform and pulse amplitudes. The waveform information would also be encoded or incorporate a look-up table so the SBS module 52 and/or 52' could select, between whether or not to deliver a sinusoidal pulse, a triangular pulse, a square wave or any other type of waveform. In the open loop communication mode, the SBS modules 52 and 52' are simply waveform generators that receive their timing and waveform type information from the control module 44. In the preferred closed loop communication mode, the SBS modules 52 and 52' continuously or intermittently sense brain wave activity and can detect the onset of an electrical storm which often precedes a seizure. These electrical storms have variable frequency content and amplitudes. The SBS modules 52 and 32' would transmit this data to the control module 44. The control module 44, in the closed loop communication mode, embodies microprocessors and software algorithms that analyze the brain activity that is being transmitted from the SBS modules 52 and 52'. If the software algorithm indicates that a seizure or other inappropriate electrical brain activity is occurring, then the microprocessors and software make a decision for the most appropriate amplitude and waveshape of the therapy pulses. The control module 44 then selects the appropriate therapy pulse waveshape, pulse repetition rates and period (timing), and sends that information via the RF communication link to the SBS modules 52 and/or 52'. The SBS modules 52 and 52' would then deliver the appropriate therapy and again monitor brain electrical activities to see if additional therapy is needed. FIG. 6 shows a closed loop communication system wherein the control module 44 can receive RF signals 54 from the SBS modules 52 and 52' transmitted as an RF pulse 56. When the control module 44 determines that there is inappropriate brain electrical activity, it transmits an RF instruction pulse 58 which is received as an RF input 60 to the SBS modules 52 and 52'.

The remote SBS modules 52 and 52' as shown in the drawings are only illustrative of a pair of deep brain stimulators. It will be appreciated that any number and various types of SBS modules can be paired with the control module 44 in accordance with the present invention. Referring once again to FIG. 6, in closed loop communication mode, deep brain signals or other biological brain signals that are sensed by the SBS modules 52 and 52' are transmitted by the RF telemetry link 56 to the control module 44. These signals can be, in turn, transmitted to an external network such as a master control center, a hospital diagnostic center or even a physician's office for analysis or diagnosis. The control modules 44 or 44' can be close coupled with a telemetry wand or RF telemetry antenna so that an external programmer 62 can be used to reprogram the control unit 44 or 44'. The external programmer 62 can also be used to store other information such as battery status, past brain electrical activity events and the like. In addition, the external programmer 62 monitors the system for malfunctions such as electrical, programming or any other faults. These errors are displayed alerting the patient or caregiver of any problems. In addition, such error codes could also be transmitted as a telemetric signal. These telemetry signals could also be transmitted or coupled to telephone lines or links and can even be provided to existing cellular telephone networks or communication systems all, for the purposes of remote monitoring, remote programming and remote diagnostics by appropriate medical personnel. The control modules 44 or 44' could also be outfitted with a GPS locator such that if the patient was having a traumatic medical event, the patient could be located and emergency medical personnel could be appropriately dispatched.

The present invention is not limited to just the stimulation and sensing of electrical signals. The remote SBS modules 52 and 52' can also be used to sense patent biologic data including cranial pressures and transmit that information back to the control module 44 or 44' as well as cerebrospinal fluid pressures (normal hydrocephalus). In other words, the present invention encompasses all aspects of continuous patient brain status and monitoring. Even real-time pulse oximetry or blood pressure monitoring can also be integrated into this overall system.

The SBS modules 52 and 52' can even be externally powered if desired. The power would be supplied by an external electromagnetic source that would couple with an internal antenna similar to an RFID chip thereby providing energy to supply the stimulation pulse. Alternatively, the external energy source could provide RE energy to recharge a battery or to recharge an energy storage capacitor. This is more fully described in U.S. Pat. No. 6,615,074, the contents of which are incorporated herein.

Figure 7:
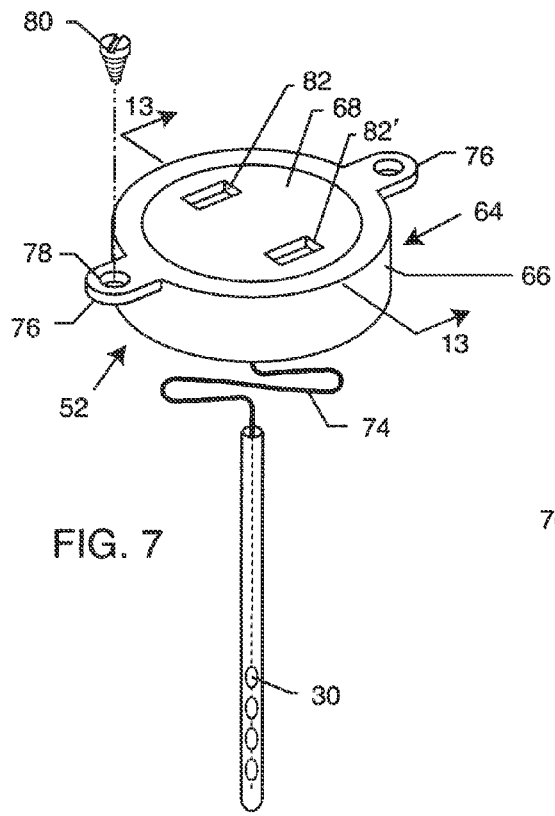
FIG. 7 is an enlarged perspective view of one of the satellite brain stimulation and/or sensing neuromodulation (SBS) modules of FIG. 6.
Figure 8:
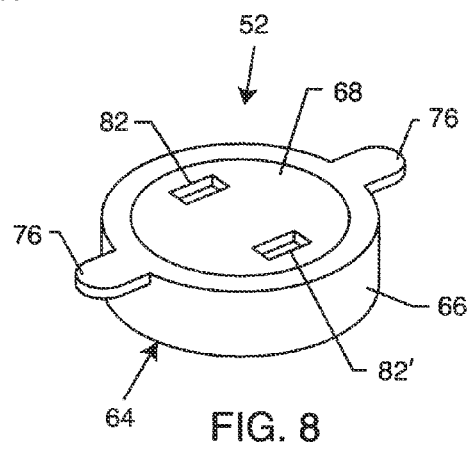
FIG. 8 is a perspective view illustrating an alternative using for the SBS module of FIG. 7.

FIG. 7 illustrates another preferred embodiment of one of the SBS modules 52. The SBS module 52 is designed to be slipped into a close fitting skull burr hole 36. The SBS module 52 comprises, generally, a biocompatible and hermetically sealed housing 64 comprised of a body 66 and a removable cap 68. Disposed within the housing 64 is a power source (shown as a battery 70 in FIG. 13) and an RF receiver or transceiver circuit 72 (FIG. 16) for wireless communication with the control module 44 or 44'. A bundle of leadwires 74 extend through the body 66 of the housing 64 and terminate at the quadpolar electrodes 30. The body 66 is further provided with a pair of tabs 76 which each may be provided with an aperture 78 therethrough (FIG. 7), or without such an aperture as illustrated in FIG. 8. The aperture 78 is provided to accommodate a skull fixation screw 80 which is utilized to help secure the housing 64 in place relative to the skull 34 and prevent twisting thereof during removal of the cap 68 from the body 66. In this regard, the cap 68 is provided with a pair or recessed slots 82 and 82'.

In the alternate embodiment of the housing 64 shown in FIG. 8, the apertures 78 through the tabs 76 for the screws 80 have been omitted. There may be instances where use of skull fixation screws 80 would be undesirable. In this case, the tabs 76 would be located within corresponding recesses 84 in the skull 34 adjacent to the formed burr-hole 36 to resist or prevent twisting of the housing body 66 when the cap 68 is screwed onto or unscrewed from the body 66.

Figure 9:
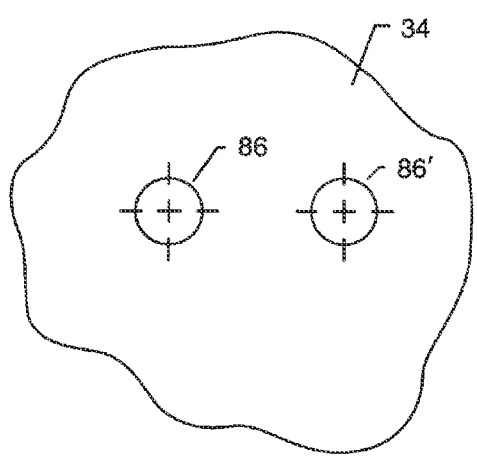
FIG. 9 is a plan view of a portion of a patient's skull illustrating the first step of a process for fitting the SBS modules of FIGS. 7 and 8.
Figure 10:
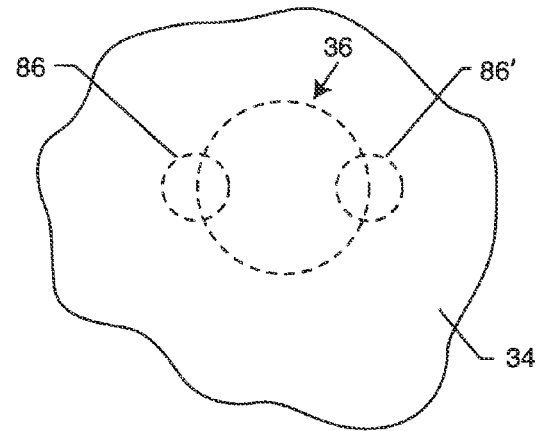
FIG. 10 is a view similar to FIG. 9, illustrating a subsequent step for preparing the skull for the remote SBS modules of FIGS. 7 and 8.
Figure 11:
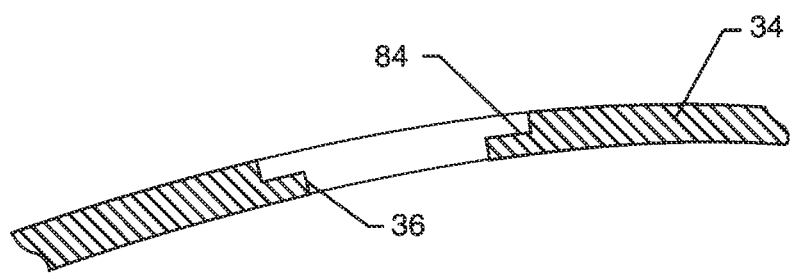
FIG. 11 is a cross-sectional view of the stepped burr hole created following the steps of FIGS. 9 and 10.
Figure 12:
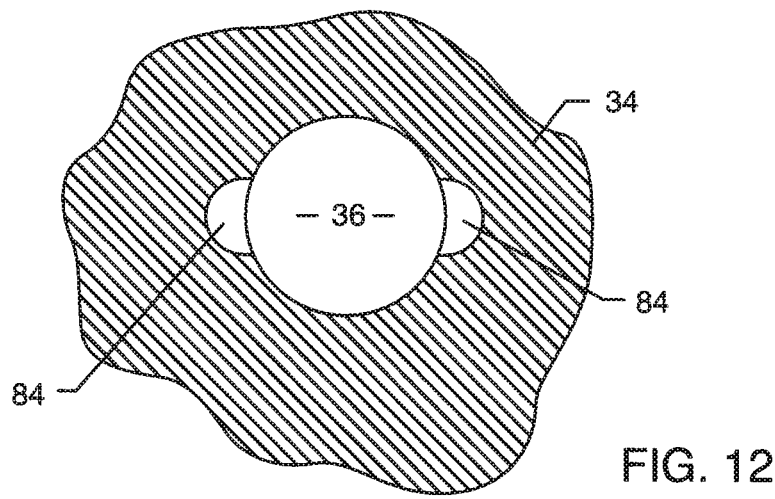
FIG. 12 is a plan view illustrating the finished stepped burr hole of FIG. 11.

Referring to FIGS. 9-12, the skull burr-hole 36 would typically be formed by first drilling two shallow recesses 86 and 86', and then a generally circular burr-hole 36 would be drilled through the skull 34 between and through a portion of each of the recesses 86 and 86' (FIGS. 9 and 10). The resultant stepped burr-hole 36 includes a passageway all the way through the skull 34 and a step or shoulder forming the recesses 84 which are configured to receive the tabs 76 of the SMS module housing 64 (see FIGS. 11 and 12). The SBS modules 52 and 52' are implanted into the skull 34 by first creating an incision in the tissue overlaying the skull to form a flap. This flap, usually with hair included, is flipped back to expose the skull. Once the SBS module 52 or 52' is affixed and its associated electrodes are implanted, the skin flap is set back in place and sutured. In a short time the suture heals. When the battery 70 needs replacement, all that is needed is a simple injection of anesthetic such as Xylocalne and a new skin flap is created to expose the cap 68. Replacing the battery 70 is as simple as removing the cap 68 and installing a new battery. It is preferable to install a new O-ring 94 and new cap 68 at each battery replacement interval to minimize the risk of complications such as infection. Battery replacement intervals vary from a few months to several years depending on the frequency of the need for therapy delivery and the amplitude and type of waveform needed.

Figure 13:
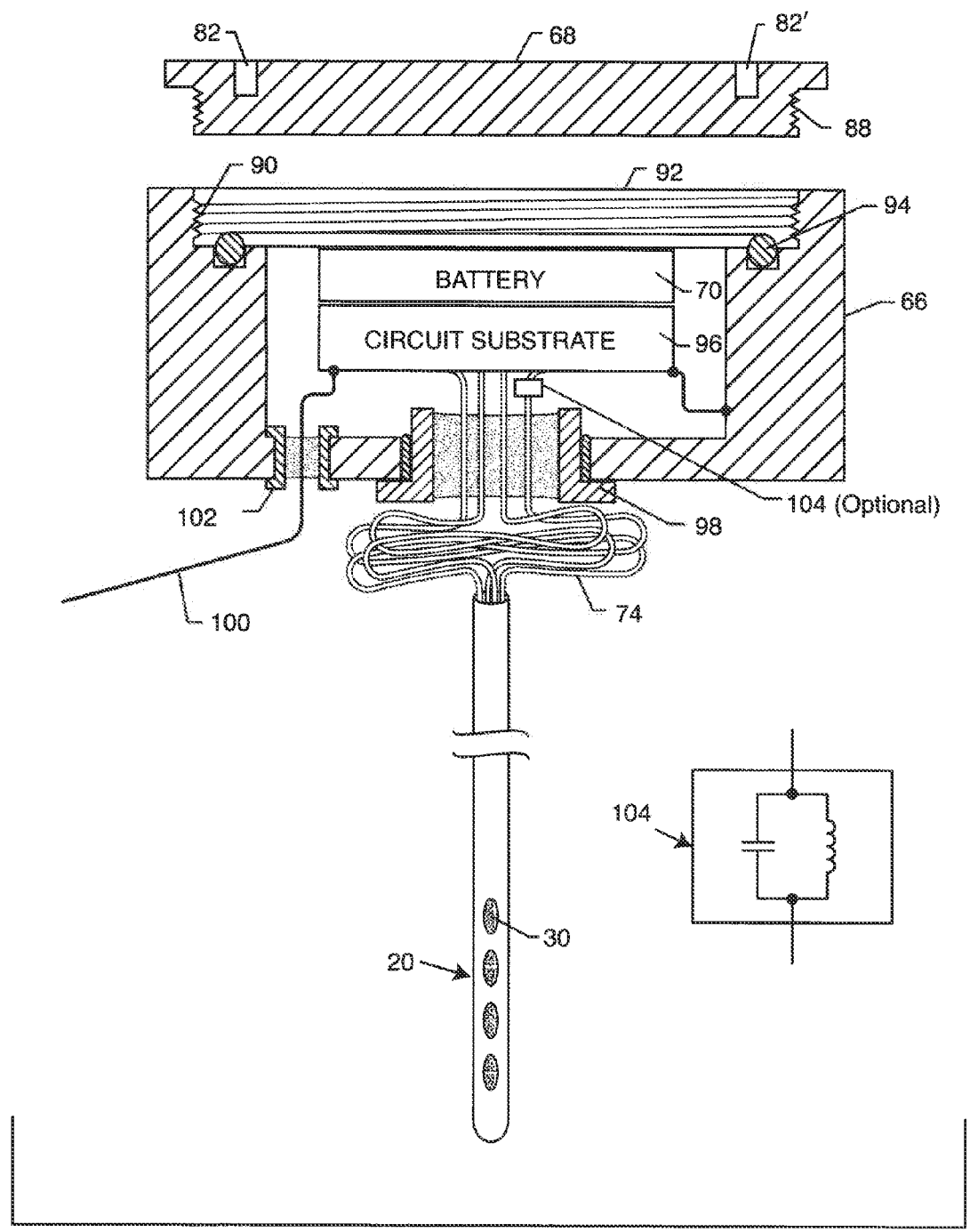
FIG. 13 is an enlarged, exploded sectional view taken generally along the line 13-13 of FIG. 7.

FIG. 13 is a cross-sectional view taken generally along the line 13-13 from FIG. 7. The cap 68 is shown removed from the body 66 of the housing 64. The upper surface of the cap 68 includes the slots 82 and 82' that are used to facilitate removal of the cap 68 from the body 66. The periphery of the cap 68 adjacent to a lower surface has threads 88 configured for mating reception with internal threads 90 defining a cap receiving recess 92 adjacent to an upper surface of the body 66. The O-ring 94 is disposed within the body 66 so that as the cap 68 is screwed into the cap receiving recess 92, a lower surface of the cap engages the O-ring 94 to form a hermetic seal between the cap 68 and the body 66.

With regard to the cap 68, it will be appreciated that the slots 82 and 82' could take a variety of shapes including a single slot, for accommodating a flat-tip screwdriver in the center of the cap, or any other shape, for example, a slot that could accommodate a cross-tip screwdriver. An important point is that the cap 68 firmly mate with the tool such that a suitable torque may be applied to unscrew the cap 68 from the body 66 and reseat it. In this regard, it is desirable that the tools utilized have torque wrench-like properties so that when the cap 68 is seated within the cap receiving recess 92, a proper compression force is applied to the O-ring 94.

Disposed within the body 66 is a circuit substrate 96 which contains the RF transceiver circuitry 72 (FIG. 16) and the pulse forming network for stimulating the electrodes 30. The control module 44 would make the decision as to which electrodes 30 or electrode pairs to stimulate, including electrical vectors between the SBS modules 52 and 52', and the like. Electrical vectors can also be generated between subcutaneous/subdural electrodes 24, or between DBS electrodes 20, as will be later described. As shown, the battery 70 is also disposed within the body 66 of the housing 64.

It is important that the O-ring 94 be of a suitable silicone, PTFE, elastomer, fluorocarbon, metal or other long-term biocompatible compressible material such that long-term hermeticity is maintained. The reason for this is for convenient replacement of the battery 70 at regular intervals. Of course, this would only be needed if the battery 70 were a primary battery and could not be recharged. The biocompatible O-ring 94 preferably has a leak rate of no more than $10^{-8}$ cubic centimeters per second. The O-ring 94 may be seated under a screw-in cap 68 as illustrated or the cap may be snapped in against a cam (not shown) and then later pried off for battery replacement. The screw-in version is the preferred embodiment. The physician battery replacement kit would include instructions and illustrations to the physician as how to locate and form the skin flap. This kit would also include a torque tool and a new cap 68 and O-ring 94. The torque tool is important to assure that the O-ring 94 is properly seated. An adjunct sealant can also be placed around the cap perimeter or over the entire cap 68 surface to provide additional sealing and biocompatibility (for example, some patients react unfavorably to titanium and may even have allergic reactions).

The O-ring 94 may be replaced or enhanced by a flexible injectable elastomer such as that described in US 2007-0168032.

In a preferred embodiment, the entire SBS module assembly would be flush with the top of the skull 34 and would be stitched under a skin flap with the hair intact. Accordingly, when the battery 70 was to be replaced, a surgeon would make a simple incision and pull back the skin flap, unscrew the cap 68 and insert a new battery. In an alternative embodiment, the top of the entire assembly could be exposed above the skull (for example, in a plastic piece or a simple plastic lid) such that battery replacement would be more convenient. This would not be as aesthetically pleasing or as comfortable for the patient, but could be an embodiment that would be chosen for elderly people or for example, people confined to convalescent home situations.

The body 66 includes a quad polar hermetic terminal 98 with four leadwires 74 that are routed down to the distal electrodes 30. The extra amount of these leadwires 74 can be spaced backwards and forwards underneath the remote SBS module housing 64. This is so that the depth of the electrodes 30 into the brain tissue can be precisely maintained and that any excess leadwire 74 can be wrapped up in the subdural area. In a preferred embodiment, the leadwires 74 are wrapped randomly or in figure eight patterns such that they not, form an efficient coupling loop for external electromagnetic field emitters (such as MRI).

Also shown is an optional RF antenna 100 coming through a second hermetic terminal 102. It will be understood that this antenna 100 could also be accommodated by the leadwire hermetic terminal 98. The RF antenna 100 can also be one of the leadwires 74 going to the electrodes 30. In fact, in a preferred embodiment, the RF antenna 100 is not needed. This is because the pacing and sensing pulses are in the low frequency biological range (0 to 2000 HZ). Accordingly, it is possible to superimpose on the leadwires 74 high frequency RF signals (for example, those in the 400 MHz range). In other words, the electrodes 30 and leadwires 74 can also simultaneously act as the RF transmitting and/or receiving antenna of the SBS modules 52 and 52' of the present invention.

The circuit substrate 96 includes RF receiving and RF transmitting circuits. When these circuits operate in conjunction with the RF antenna 100, this forms what is known as an RF transceiver. An RF transceiver is required for the closed loop communication mode. In the open loop communication mode, the circuit substrate 96 would have an RF receiver only and the pulse forming network would be responsive to control signals from the control module 44. In the closed loop communication mode/embodiment, the transceiver of the SBS module 52 would communicate with the transceiver of the control module 44 such that electrical brain wave activity is monitored and appropriate therapy is selected.

FIG. 13 also shows an optional bandstop filter module 104. This could be placed in series with each leadwire 74 to act as a very high impedance at the selected frequencies of certain medical diagnostic equipment. In particular, during magnetic resonancing procedures, the leads and electrodes are exposed to a very powerful pulsed RF field. By properly selecting the values of inductance and capacitance, one can cause the circuit to be resonant at the pulsed resonant frequency of an MRI system. This would create a very high impedance at that frequency and thereby stop the flow of current into the leadwires 74. It would also act as a very important protection to the microelectronics located on the circuit substrate 96. The bandstop filter 104 could be replaced by electronic switches, MEMs switches, multiplexers or a short to housing. Also provided are diode protection arrays 106 (FIG. 16) to protect the circuit electronics from over-voltages caused by the patient coming into contact with electrostatic discharges, automatic external defibrillators (AEDs), and the like. See U.S. Pat. No. 7,363,090 and U.S. Patent Publication Nos. 2007-0112398 A1, 2008-0071313 A1, 2008-0049376 A1, 2008-0132987 A1, 2008-0116997 A1, and 2008-0161886 A1, the contents of all of which are incorporated herein by reference.

The circuit substrate 96 could be a rigid substrate consisting of alumina ceramic, FR-4 board, or even a flexible substrate. A preferred embodiment would be to use a polyimide flex substrate designed for robotic placement and manufacturing of components. The automated manufacturing system would be fed from tape and reel components wherein pick-and-place robots would place the components which then go through an automated wave soldering operation followed by a cleaning operation then by an automated microscopic optical tolerance position measurement (quality control), followed by automated electrical measurements.

The entire housing 64 could either be of a biocompatible material such as titanium, platinum or other suitable biocompatible metal. Pressed powder metallurgy, machining techniques or the like can be used to form these shapes. The housing 64 could also be of a high fired or low fired ceramic construction such as nearly pure alumina ceramic. The process would involve tools (fixtures) into which powdered alumina would be pressed. Then the shapes would be fired at high temperature so that the ceramic is sintered into a hard body. Leads could either be co-fired or later gold brazed into lead penetration holes. This eliminates the need for separate hermetic terminals 98 and 102. The interior of the ceramic body could be metalized with a thin coating of metal to provide suitable electromagnetic interference shielding and protection.

Figure 14:
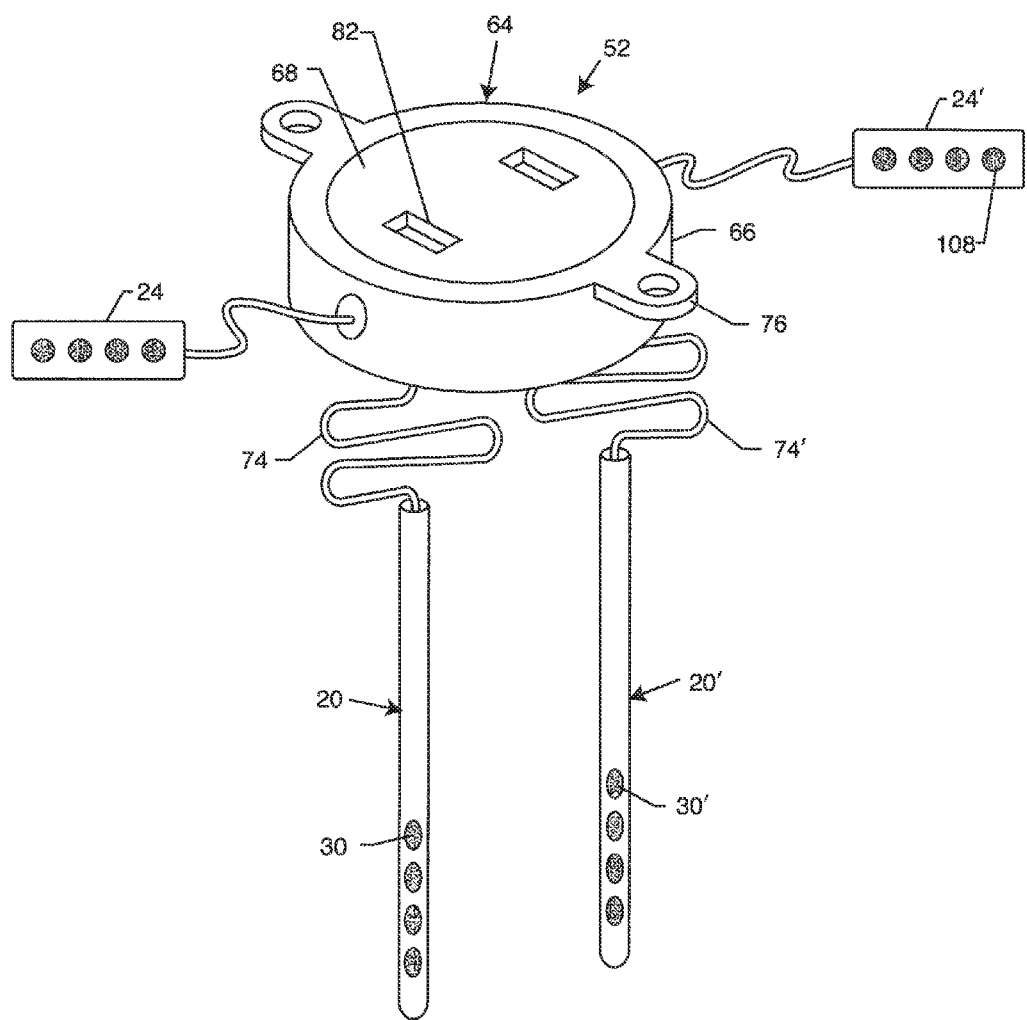
FIG. 14 is a view similar to FIGS. 7 and 13, illustrating an alternative embodiment of a remote SBS module.

FIG. 14 illustrates an alternative embodiment of an SBS module 52. One can see that there is a pair of DBS electrodes 20 and 20'. These are both connected to a single SBS module 52 as shown. Also shown are remote paddle electrodes 24 and 24'. These would be typically placed between the skin and the skull or even under the skull. The purpose of this is so that the implanting physician has a number of options as to vectors for sensing brain activity or vectors for providing brain stimulation pulses. In other words, one could stimulate or sense between any of the electrode pairs 30 or 30' or between, for example, the DBS electrode 20 and the paddle electrode 24, or even between the individual electrodes 30 of the DBS electrode 20. Likewise, one could stimulate or sense between any of the individual electrodes 108 of the paddle electrode 24'.

Figure 15:
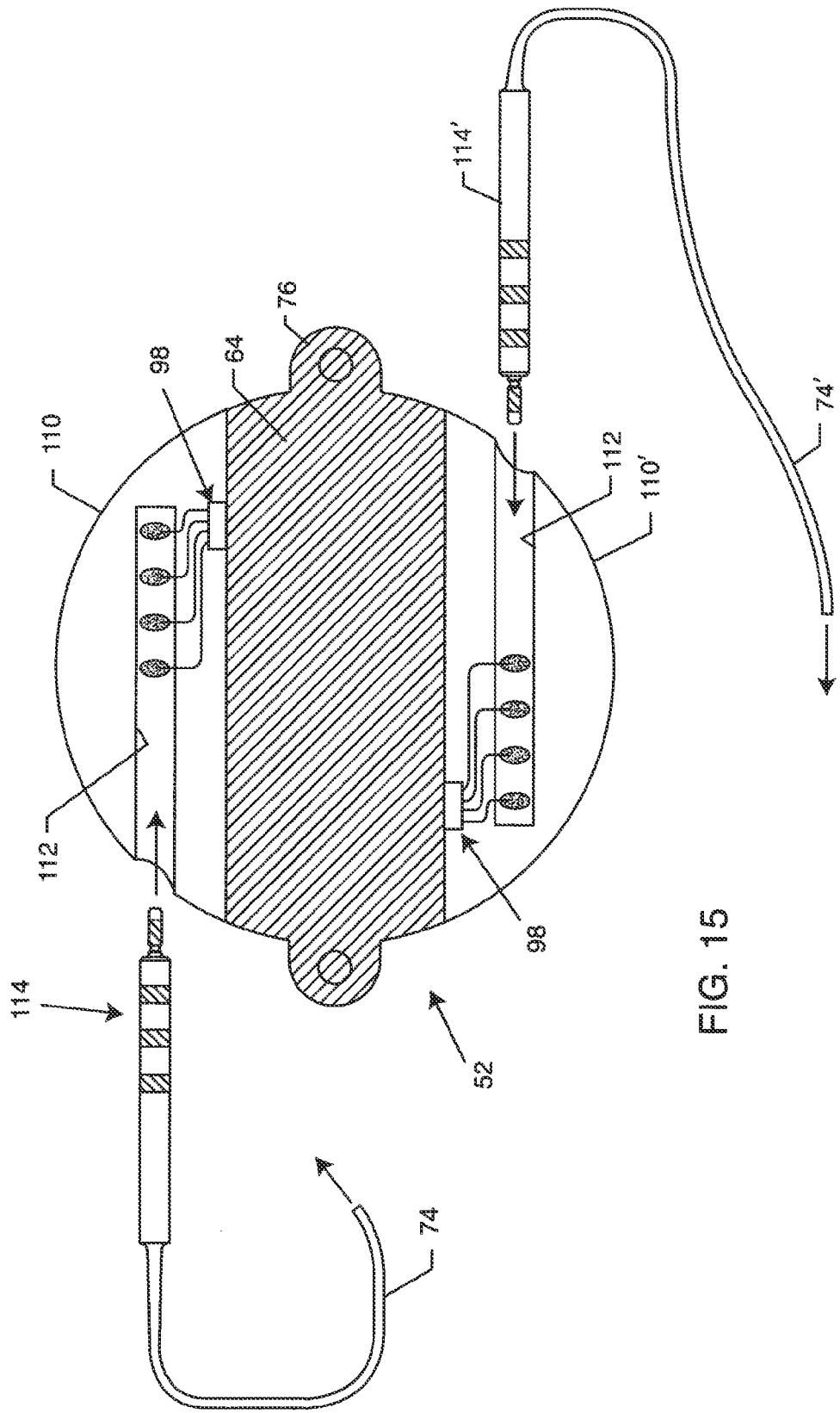
FIG. 15 illustrates an alternative embodiment similar to FIG. 14.

FIG. 15 illustrates another alternative embodiment of the present invention. The SBS module 52 consists of a titanium or alumina housing 64 with two connector block assemblies 110, 110'. The connector block assemblies 110 and 110' each have an inline receptacle 112 that is very similar to pacemaker standard International Standards Organization (ISO) IS-4. Also shown are IS-4 type proximal mating plugs 114 and 114' which are attached to leads 74 and 74' and then to a DBS electrode assembly in accordance with the present invention. The advantage of the structure of FIG. 15 is that the entire SBS module 52 can be placed into a specially formed skull burr hole 36 and then leads 74 and 74' can be routed in such a way to provide the stimulus into brain tissue as required. Once the primary battery was depleted or the electronics failed in the SBS module 52, it could be removed and a new one could simply be plugged into the existing leads 74 and 74'. This is a relatively easy procedure compared to the extremely invasive procedure that would be required to remove the DBS electrodes 20 and 20' which could result in brain tissue trauma. However, the burr hole 36 would be very complicated and would require a great deal of milling and machining. In other words, it is not a simple drilling operation of round holes using bore fixtures as shown in FIGS. 9-12.

Figure 16:
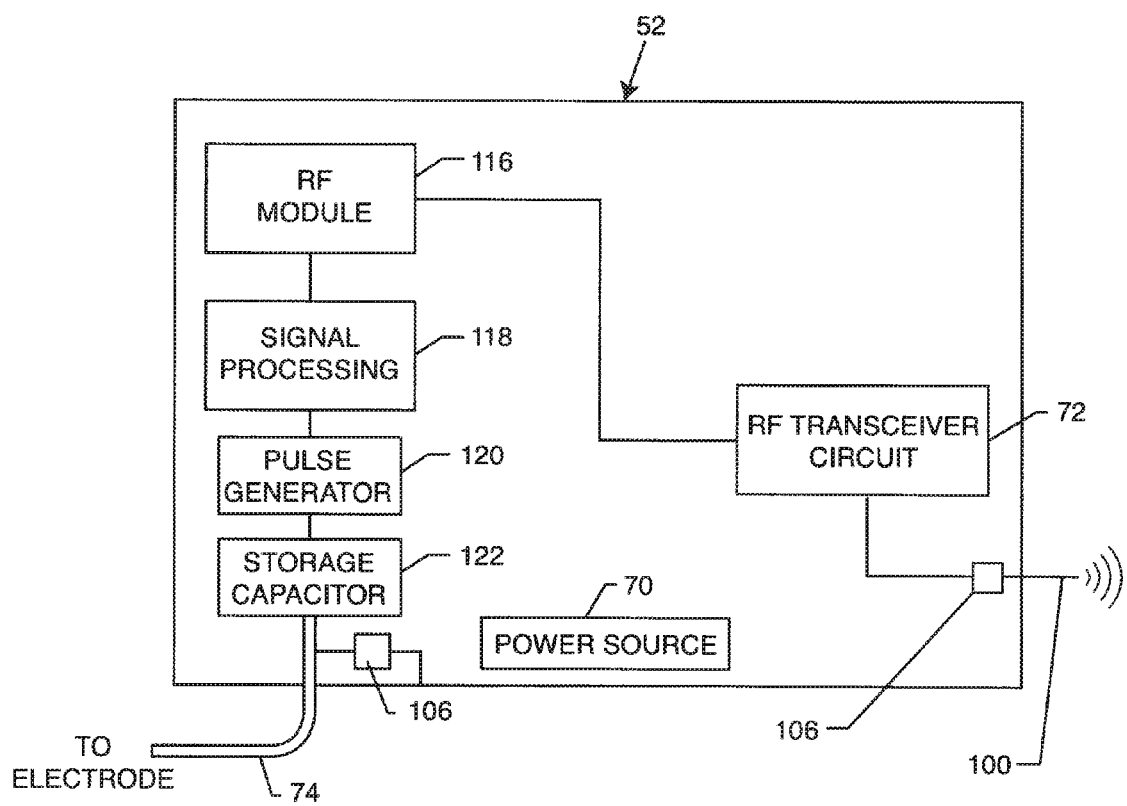
FIG. 16 is a block diagram of a control and telemetry system for the remote SBS module of the present invention.

FIG. 16 is a block diagram of a control and telemetry system of the closed loop embodiment of the SBS module 52. The circuit board 96 will have a RF transceiver circuit 72, an RF module 116, a signal processing circuit 118, and a pulse generator circuit 120 capable of producing various pulse shapes and repetition rates. This transceiver circuit 72 is designed to send and receive RF signals that are modulated to communicate with the control module 44. Not shown are capacitors in series with each electrode to prevent any DC bias from being conducted from the circuit boards to human tissue. The RF signals, in a preferred embodiment, are digitally modulated or frequency shift keyed in order to be able to transmit sensed brain wave information from the SBS module 52 to the control module 44. In turn, similar modulation is used for the RF signals that are transmitted by the control module 44 to control the wave shape and repetition rate that is delivered to the brain electrodes by the SBS module 52. Since the SBS module 52 is preferably very small in size, it will have very limited microprocessor capability. In a preferred embodiment, in its architecture would be stored a look-up table. In this way, a simple lettered digital code could be received from the main control module 44. For example, if an alpha numeric A12 was received by the SBS module 52, its look-up table would tell it to deliver, for example, a triangular pulse sequence with a repetition rate of 10 beats per minute and an amplitude of 4 millivolts. By having look-up tables stored into hard memory, one not only greatly decreases the amount of memory in software that must be contained within the SBS module 52, but one also saves significant battery life. The reason for this is that the RF transmission bursts can be very short as compared to sending a lot of information, such as sending exact pulse shape and timing information. A storage capacitor 122 is further provided so that a sufficient stimulation pulse may be generated on command as required by the control module 44. As mentioned previously, protection diode arrays 106 may also be provided.

From the foregoing, it will be appreciated that the satellite therapy delivery system for brain neuromodulation comprises a control module including an RF transmitter or transceiver, and a satellite brain stimulation and/or sensing (SBS) module including biologic stimulating and/or sensing electrodes, a power source, and an RF receiver or transceiver for wireless communication with the control module. The control module 44 may be implanted within a patient's body at a location remote from the SBS modules 52 and 52', or it may be externally worn by the patient. The stimulating and/or sensing electrodes of the SBS modules 52 and 52' may include DBS electrodes 20 and 20', and/or subcutaneous or subdural paddle, patch or pad electrodes 24 and 24'. The SBS modules 52 and 52' comprise biocompatible and hermetic sealed housings preferably fixed within a burr-hole through a patient's skull. The satellite therapy delivery system of the present invention lends itself to both open loop communication between the control module 44 and the satellite modules 52 and 52', and closed loop communication between those same components. Advantageously, the housing 64 for the SBS modules 52 and 52' includes a removable cap 68 which permits easy access to a battery 70 normally disposed therein.

Although several particular embodiments of the invention have been described in detail for purposes of illustration, various modifications may be made without departing from the spirit and scope of the invention. Accordingly, the invention is not to be limited, except by the appended claims.

What is claimed is:

1. A satellite therapy delivery system for brain neuromodulation, comprising:
   a) a satellite brain stimulation and/or sensing (SBS) module comprising:
      i) at least one biologic stimulating and sensing electrode;
      ii) an SBS housing;
      iii) a first electrical power source disposed within the SBS housing;
      iv) a first RF transceiver disposed within the SBS housing and powered by the first electrical power source; and
      v) an SBS processing circuit powered by the first electrical power source, wherein the SBS processing circuit is electrically connected to the first RF transceiver;
   b) a control module capable of analyzing an SBS RF wireless signal, the control module comprising:
      i) a control module housing;
      ii) a second electrical power source;
      iii) a second RF transceiver; and
      iv) a microprocessor,
      v) wherein the second RF transceiver and the microprocessor are disposed within the control module housing and powered by the second electrical power source,
   c) wherein the SBS housing is positionable within a burr hole through a patient's skull,
   d) wherein the at least one electrode is actuatable by the SBS processing circuit in response to an RF wireless signal having been firstly received by the SBS module and secondly analyzed by the control module,
   e) wherein the SBS module is configurable for RF wireless transmission of sensed biologic data from the at least one electrode to the control module,
   f) wherein the control module is configurable to process transmitted biologic data to determine if therapy is required, and wherein when therapy is required, actuation instructions are transmittable by the control module to the SBS module, and
   g) wherein the actuation instructions that are transmittable by the control module to the SBS module comprise instructions to actuate stimulation timing and stimulation waveform of the at least one electrode.

2. The system of claim 1, wherein the control module is not implanted within a skull of a patient.

3. The system of claim 1, wherein the control module is configurable to be externally worn by a patient having an implanted SBS module.

4. The system of claim 1, wherein the at least one electrode is selected from the group consisting of a deep brain electrode, and a subcutaneous or subdural paddle, patch or pad electrode.

5. The system of claim 1, wherein the control module and the SBS module are configurable to operate in an open loop communication mode.

6. The system of claim 1, wherein the control module and the SBS module are configurable to operate in a closed loop communication mode.

7. The system of claim 1, wherein the SBS module comprises a plurality of SBS modules, each SBS module being configurable to communicate independently with the control module through wireless communication.

8. The system of claim 7, wherein the plurality of SBS modules are configurable to communicate independently with each other through wireless communication.

9. The system of claim 1, wherein the SBS module comprises a pulse generator.

10. The system of claim 1, wherein the control module is configurable to communicate with an external programmer or network through telemetric wireless communication.

11. The system of claim 10, wherein the control module is configured to permit telemetric transmission of patient data to the external programmer or network.

12. The system of claim 11, wherein the transmitted patient data is selected from the group consisting of GPS data, current or historical-sensed patient biologic data, and current or historical therapy delivery data.

13. The system of claim 1, wherein the at least one electrode is a stimulating electrode that is actuatable by the SBS processing circuit in response to a signal received from the control module.

14. The system of claim 1, wherein the SBS module is configurable to intermittently transmit sensed biologic data from the at least one electrode as a biological sensing electrode to the control module.

15. The system of claim 14, wherein the SBS module is configurable to transmit the sensed biologic data to the control module only when pre-defined biologic data is detected by the SBS module.

16. The system of claim 1, wherein the SBS housing is fixable to a patient's skull utilizing screws to prevent twisting of the SBS housing.

17. The system of claim 1, wherein the SBS housing comprises fixation tabs that are disposable within corresponding burr-hole recesses.

18. The system of claim 1, wherein the SBS housing comprises a ceramic housing.

19. The system of claim 18, wherein the ceramic housing comprises an alumina ceramic housing.

20. The system of claim 1, wherein a lead for the at least one electrode and/or for an antenna extends through the SBS housing.

21. The system of claim 20, wherein the SBS housing comprises a hermetic terminal through which the lead extends.

22. The system of claim 1, wherein the SBS housing comprises at least one hermetic terminal through which a lead electrically connected to the at least one electrode extends.

23. The system of claim 1, wherein a circuit board is disposed within the SBS housing, the circuit board comprising the first RF transceiver and being electronically connected to the first power source, the at least one electrode, and an RF antenna.

24. The system of claim 1, wherein the at least one electrode serves as an RF antenna.

25. The system of claim 1, wherein the SBS housing comprises an exterior receptacle for an electrode lead plug, and wherein the exterior receptacle is configured to provide an electrical connection through the SBS housing from a lead extending from a lead distal end electrically connected to the at least one electrode to a lead proximal plug end received in the receptacle and then to a circuit board disposed within the SBS housing.

26. The system of claim 1, wherein the first electrical power source and the second electrical power source are replaceable.

27. A satellite therapy delivery system for brain neuromodulation, comprising:

a) a satellite brain stimulation and/or sensing (SBS) module comprising:
  i) at least one biologic stimulating electrode;
  ii) at least one sensing electrode;
  iii) an SBS housing;
  iv) a first electrical power source disposed within the SBS housing;
  v) a first RF transceiver disposed within the SBS housing and powered by the first electrical power source; and
  vi) an SBS processing circuit powered by the first electrical power source, wherein the SBS processing circuit is electrically connected to the first RF transceiver;
b) a control module capable of analyzing an SBS RF wireless signal, the control module comprising:
  i) a control module housing;
  ii) a second electrical power source;
  iii) a second RF transceiver; and
  iv) a microprocessor,
  v) wherein the second RF transceiver and the microprocessor are disposed within the control module housing and powered by the second electrical power source,
c) wherein the SBS housing is positionable within a burr hole through a patient's skull,
d) wherein the sensing electrode is actuatable by the SBS processing circuit in response to an RF wireless signal having been firstly received by the SBS module and secondly analyzed by the control module,
e) wherein the SBS module is configurable for RF wireless transmission of sensed biologic data from the at least one sensing electrode to the control module,
f) is wherein the control module is configurable to process transmitted biologic data to determine if therapy is required, and wherein when therapy is required, actuation instructions are transmittable by the control module to the SBS module, and
g) wherein the actuation instructions that are transmittable by the control module to the SBS module comprise instructions to actuate stimulation timing and stimulation waveform of the at least one stimulation electrode.

28. A satellite therapy delivery system for brain neuromodulation, comprising:

a) a satellite brain stimulation and/or sensing (SBS) module comprising:
  i) at least one leadwire physically and electrically connected to at least one biologic stimulating and/or sensing electrode;
  ii) an SBS housing;
  iii) a first electrical power source disposed within the SBS housing;
  iv) a first RF transceiver disposed within the SBS housing and powered by the first electrical power source; and
  v) an SBS processing circuit powered by the first electrical power source, wherein the SBS processing circuit is electrically connected to the first RF transceiver;
b) a control module capable of analyzing an SBS RF wireless signal, the control module comprising:
  i) a control module housing;
  ii) a second electrical power source;
  iii) a second RF transceiver; and
  iv) a microprocessor, v) wherein the second RF transceiver and the microprocessor are disposed within the control module housing and powered by the second electrical power source, c) wherein the SBS housing is positionable within a burr hole through a patient's skull, d) wherein the at least one electrode is actuatable by the SBS processing circuit in response to an RF wireless signal having been firstly received at the SBS module from the at least one leadwire serving as an RF antenna and secondly analyzed by the control module, e) wherein the SBS module is configurable for RF wireless transmission of sensed biologic data from the at least one electrode to the control module, f) wherein the control module is configurable to process transmitted biologic data to determine if therapy is required, and wherein when therapy is required, actuation instructions are transmittable by the control module to the SBS module, and g) wherein the actuation instructions that are transmittable by the control module to the SBS module comprise instructions transmitted along the at least one leadwire to actuate stimulation timing and stimulation waveform of the at least one electrode.

* * * * *

UNITED STATES PATENT AND TRADEMARK OFFICE
CERTIFICATE OF CORRECTION

PATENT NO. : 8,792,987 B2
APPLICATION NO. : 13/858268
DATED : July 29, 2014
INVENTOR(S) : Robert A. Stevenson et al.

It is certified that error appears in the above-identified patent and that said Letters Patent is hereby corrected as shown below:

In the Claims,

Column 16, line 35 (Claim 27, line 35) after "f)" delete the word "is"

Signed and Sealed this
Twenty-fourth Day of February, 2015

Michelle K. Lee
*Deputy Director of the United States Patent and Trademark Office*